United States Patent
Raab et al.

(10) Patent No.: US 9,775,949 B2
(45) Date of Patent: Oct. 3, 2017

(54) CARTRIDGE HOLDER, DRUG DELIVERY DEVICE AND METHOD FOR SECURING A CARTRIDGE IN A CARTRIDGE HOLDER

(75) Inventors: Steffen Raab, Frankfurt am Main (DE); Sandra Arnhold, Büttelborn (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 961 days.

(21) Appl. No.: 13/575,353

(22) PCT Filed: Jan. 31, 2011

(86) PCT No.: PCT/EP2011/051306
§ 371 (c)(1),
(2), (4) Date: Sep. 24, 2012

(87) PCT Pub. No.: WO2011/092326
PCT Pub. Date: Aug. 4, 2011

(65) Prior Publication Data
US 2013/0046245 A1   Feb. 21, 2013

(30) Foreign Application Priority Data

Feb. 1, 2010  (EP) .................................. 10152219

(51) Int. Cl.
*A61M 5/00* (2006.01)
*A61M 5/24* (2006.01)
(Continued)

(52) U.S. Cl.
CPC .............. *A61M 5/24* (2013.01); *A61M 5/3134* (2013.01); *A61M 5/347* (2013.01); *A61M 2005/2437* (2013.01); *A61M 2005/2488* (2013.01)

(58) Field of Classification Search
CPC ............ A61M 5/24; A61M 2005/2407; A61M 2005/2488; A61M 2005/2437
See application file for complete search history.

(56) References Cited

U.S. PATENT DOCUMENTS 5,002,537 A    3/1991  Hoffman et al.
5,549,575 A *  8/1996  Giambattista ........... A61M 5/24
                                                              604/206
(Continued)

FOREIGN PATENT DOCUMENTS

EP   1681070   7/2006
FR   2026134   9/1970
(Continued)

OTHER PUBLICATIONS

International Search Report for Int. App. No. PCT/EP2011/051306, mailed May 2, 2011.
(Continued)

*Primary Examiner* — Emily Schmidt
(74) *Attorney, Agent, or Firm* — McDonnell Boehnen Hulbert & Berghoff LLP (57) ABSTRACT

A cartridge holder, which has a distal end and a proximal end, comprises a coupling housing portion in which a cartridge can be inserted at least partly. The coupling housing portion is configured to be coupled to a part of a drug delivery device. The cartridge holder further comprises a fixing member which is connected with the coupling housing portion. The fixing member is moveable radially inwardly to a position in which the fixing member is suitable for securing the cartridge against distal displacement of the cartridge.

13 Claims, 6 Drawing Sheets

(51) Int. Cl.
     *A61M 5/31*  (2006.01)
     *A61M 5/34*  (2006.01)

(56) References Cited

U.S. PATENT DOCUMENTS

| | | | |
|---|---|---|---|
| 5,693,027 A | | 12/1997 | Hansen et al. |
| 5,921,966 A | * | 7/1999 | Bendek .................. A61M 5/24 |
| | | | 604/207 |
| 6,036,675 A | | 3/2000 | Thorne et al. |
| 2003/0109834 A2 | | 6/2003 | Bitdinger et al. |
| 2004/0108339 A1 | | 6/2004 | Hansen et al. |
| 2009/0312715 A1 | | 12/2009 | Monson et al. |
| 2011/0092917 A1 | * | 4/2011 | Wei et al. ..................... 604/241 |
| 2011/0288493 A1 | * | 11/2011 | Holmqvist .............. A61M 5/24 |
| | | | 604/241 |
| 2012/0143143 A1 | * | 6/2012 | Giambattista ....... A61M 5/2033 |
| | | | 604/192 |

FOREIGN PATENT DOCUMENTS

| | | |
|---|---|---|
| WO | 99/16487 | 4/1999 |
| WO | 2007/104636 | 9/2007 |
| WO | 2009/137486 | 11/2009 |
| WO | 2011/092326 | 8/2011 |

OTHER PUBLICATIONS

International Preliminary Report on Patentability for Int. App. No. PCT/EP2011/051306, mailed Jun. 12, 2012.
Examination Report from the Intellectual Property Office of Singapore for App. No. 201205703-0, mailed Feb. 17, 2015.
Chinese Office Action for CN Application No. 201410737061.6, issued Jul. 18, 2016.
Japanese Appeal Judgment for JP Application No. 2015-19551, dated Aug. 28, 2016.

* cited by examiner

CARTRIDGE HOLDER, DRUG DELIVERY DEVICE AND METHOD FOR SECURING A CARTRIDGE IN A CARTRIDGE HOLDER

CROSS REFERENCE TO RELATED APPLICATIONS

The present application is a U.S. National Phase Application pursuant to 35 U.S.C. §371 of International Application No. PCT/EP2011/051306 filed Jan. 31, 2011, which claims priority to European Patent Application No. 10152219.1 filed on Feb. 1, 2010. The entire disclosure contents of these applications are herewith incorporated by reference into the present application.

FIELD OF INVENTION

The invention concerns a cartridge holder, a drug delivery device comprising a cartridge holder and a method for securing a cartridge in a cartridge holder.

BACKGROUND

A drug delivery device is operable to deliver a drug from a cartridge, for example via a cannula. The cartridge is located in a cartridge holder which is part of the drug delivery device. A dose setting and delivery mechanism of the drug delivery device pushes a bung in the distal direction along the inner wall of the cartridge so that a dose of drug is delivered.

If the cartridge is not connected with the dose setting and delivery mechanism or the housing of the drug delivery device, the cartridge may be axially disposable with respect to the dose setting and delivery mechanism. Even a slight mobility of the cartridge may cause underdosing or overdosing of the drug.

It is an aim of the present invention to reduce the risk of underdosing or overdosing.

SUMMARY

For this aim a cartridge holder is provided. The cartridge holder which has a distal end and a proximal end comprises a coupling housing portion in which a cartridge can be inserted at least partly. The coupling housing portion is configured to be coupled to a part of a drug delivery device. The cartridge holder further comprises a fixing member which is connected with the coupling housing portion, the fixing member being moveable radially inwardly to a position in which the fixing member is suitable for securing the cartridge against distal displacement of the cartridge.

A cartridge which is at least partly located inside the coupling housing portion of the cartridge holder is secured when the fixing member is moved inwardly, which means that the fixing member is moved towards the cartridge. The movement of the fixing member may be caused by a force impact to an outer side of the fixing member.

The fixing member serves to lock the cartridge in place in the drug delivery device. A cartridge holder which comprises the fixing member is suitable for securing the cartridge, thereby reducing the mobility of the cartridge inside the cartridge holder, so that the exact dose is delivered.

The drug delivery device is a single-dose or multi-dose, disposable or re-usable device designed to dispense a selected dose of a drug, preferably multiple selected doses, e.g. insulin, human growth hormones, heparins and their analogues and/or derivates. The device may be of any shape, e.g. compact or pen-type. A pen-type device is an elongate device which may be essentially cylindrical or be formed like an ellipsoid. Dose delivery may be provided through a mechanical or electrical drive mechanism or a stored energy drive mechanism. In one embodiment the drug delivery device comprises a needle unit for injection.

The cartridge is a container for the drug. The cartridge may be replaceable in a re-usable device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39), des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge holder is a part of the drug delivery device in which the cartridge is at least partly located. The cartridge holder may be designed to hold and protect the cartridge so that the cartridge holder may serve as housing for the cartridge. In one embodiment the cartridge holder is essentially tubular-shaped. The cartridge holder may comprise side walls which at least partly surround a space which is provided for the cartridge, wherein the walls are arranged so that the cartridge is hold inside the cartridge holder.

The coupling housing portion is a portion of the cartridge holder in which a part of the cartridge can be positioned. In one embodiment the distal part of the cartridge can be located in the coupling housing portion. In an alternative embodiment a proximal part of the cartridge can be located in the coupling housing portion. The coupling housing portion is configured to be coupled to another part of the drug delivery device. "To be coupled" means interlocking of two or more components of the drug delivery device, for example by a spline, snap or thread connection. In one embodiment the coupling housing portion of the cartridge holder is inserted in another part of the drug delivery device, for example by screwing. In an alternative embodiment the coupling housing portion is inserted in another part of the drug delivery device and coupled by snapping means or any other suitable coupling means. Preferably, the coupling housing portion is located at the distal or proximal ends of the cartridge holder.

The fixing member is coupled to the coupling housing portion so that the fixing member is moveable radially inwardly with respect to the cartridge holder or the coupling housing member, which means that the fixing member can be moved towards the longitudinal axis of the cartridge holder. In other words, the fixing member is moveable into the space which is provided for the cartridge or towards the cartridge, if it is inserted in the cartridge holder. Preferably, the fixing member is in an initial position before moving it inwardly, so that the cartridge can be inserted into the cartridge holder. When the fixing member is moved radially inwardly, the cartridge is secured by positive locking and/or force closure between the fixing member and the cartridge. In one embodiment the fixing member has an inner side and an outer side, wherein the fixing member is moveable radially inwardly with respect to the cartridge holder so that the inner side abuts on a cartridge when a force impacts on the outer side. One embodiment of the cartridge holder comprises at least two fixing members, which are positioned essentially equally spaced on a periphery of the coupling housing portion. If two fixing members are provided they are preferably located opposite to each other. If three fixing members are provided the angular distance between two of them is 120 degrees or about 120 degrees.

Securing the cartridge means fixing the cartridge in such a manner that distal displacement is hindered or prevented. Preferably proximal displacement is also hindered or prevented.

The distal end is close to the dispersion end of the drug delivery device. The proximal end is furthest away from the distal end of the drug delivery device.

In one embodiment of the cartridge holder the fixing member is flexible and integrally formed with the coupling housing portion. Flexible means that the fixing member is elastically deformable. The movement of the fixing member is reversible when a force no longer impacts on the fixing member. A cartridge having a coupling housing portion which is integrally formed with the fixing member may be formed in a single step. One embodiment of such cartridge holder is made of plastics.

In one embodiment the fixing member has an outer side, an inner side and a side which is connected with the coupling housing portion. An edge of the fixing member extends from one end of the side which is connected with the coupling housing portion to the other end of this side. The edge may be rounded, for example semicircular. Alternatively, the edge may have one corner or more corners, so that the fixing member has a triangular or rectangular form for example. The edge is separated from the coupling housing portion by a cut-out. This fixing member is a wall section of the coupling housing member which can be bent inwardly.

In one embodiment the coupling housing portion comprises a thread, which is a full or part thread located on the external surface of the coupling housing portion. The thread may be formed by a helical structure, e.g. a rib or a groove, which allows rotational and axial movement of the coupling housing member with respect to the part of the drug delivery device to which the coupling housing member is to be attached.

In one embodiment the fixing member comprises a first protrusion formed on the outer side of the fixing member. The fixing member is moved radially inwardly when a force impacts on the first protrusion. The first protrusion may protrude over the part of the coupling housing member which surrounds the first protrusion. In an embodiment the coupling housing member has a thread which is formed by ribs, wherein the first protrusion protrudes over the ribs. In an alternative embodiment the coupling housing member has a thread which is formed by trenches, the first protrusion protrudes over the outside wall in which the trenches are formed. When the coupling housing member is inserted to the part of the drug delivery device to which the coupling housing member shall be coupled the inner wall of the part of the drug delivery device abuts on the first protrusion, thereby inwardly moving the fixing member so that the cartridge is secured.

In one embodiment the fixing member comprises a catch portion formed on the inner side of the fixing member. The catch portion abuts on and/or engages with the cartridge so that its distal displacement is hindered or prevented because of friction and/or positive locking Preferably, proximal displacement is also hindered or prevented.

In one embodiment the coupling housing portion is configured to be coupled with a needle unit. The needle unit which comprises a cannula is configured to be connected with the distal part of the cartridge holder. Preferably, a new needle unit is attached to the cartridge holder before each delivery process.

In one embodiment the coupling housing portion is configured to be coupled with a body member of the drug delivery device. The body member may be a proximal part of the drug delivery device which comprises any exterior or interior housing. The body member may be designed to house, fix, protect, guide and/or engage with inner components of the drug delivery device, for example a dose setting and delivery mechanism. The body member may be unitary or a multipart component.

An embodiment of the drug delivery device comprises an embodiment of a cartridge holder as described above and a cartridge which is located in the cartridge holder. A part of the drug delivery device is coupled with the coupling housing portion, wherein the fixing member is positioned in the position so that the cartridge is secured against distal displacement. Securing the cartridge against distal displacement ensures that the piston rod remains in touch with the cartridge bung, which prevents delivery of a wrong dose. Preferably, the cartridge is also secured against proximal displacement.

In one embodiment of the drug delivery device the coupling housing portion is inserted to the part of the drug delivery device which is coupled with the coupling housing portion. The inside wall of this part of the drug delivery device abuts on the fixing member, thereby inwardly bending it. One embodiment of the part of the drug delivery device which is coupled with the cartridge holder comprises a second protrusion which abuts on the fixing member. If the fixing member has a first protrusion, the second protrusion may abut on the first one.

In one embodiment of the drug delivery device the fixing member is configured to engage with a cavity provided in the cartridge or a necking of the cartridge. The necking is a circumferential concave section of the cartridge, e.g. a circumferential trench. In one embodiment the necking is a neck portion of the cartridge which is located between the distal end which is formed as skirt and a body portion of the cartridge, the skirt protruding over the neck portion, which means the diameter of the skirt is larger than the diameter of the neck portion. In one embodiment the fixing member is configured to engage with the neck portion, thereby securing the cartridge. Preferably, the cartridge is secured when the needle unit is attached, thereby at least partly engaging the fixing member with the neck portion of the cartridge.

In another embodiment the fixing member is suitable for abutting on the cartridge, thereby forming a force-fit connection between the cartridge and the fixing member. The force-fit connection is provided when the fixing member is pushed towards the cartridge. In an alternative embodiment a positive connection is provided when the fixing member is pushed towards the cartridge.

A method for securing a cartridge in a cartridge holder which comprises a coupling housing portion and a fixing member being connected with the coupling housing portion comprises the following steps. The cartridge is inserted into the cartridge holder so that the cartridge is at least partly inserted in the coupling housing portion of the cartridge holder. The coupling housing portion is coupled with a part of a drug delivery device, so that the fixing member moves radially inwardly to a position in which the fixing member secures the cartridge against distal displacement of the cartridge.

Other features will become apparent from the following detailed description when considered in conjunction with the accompanying drawings.

DETAILED DESCRIPTION

Figure 1:
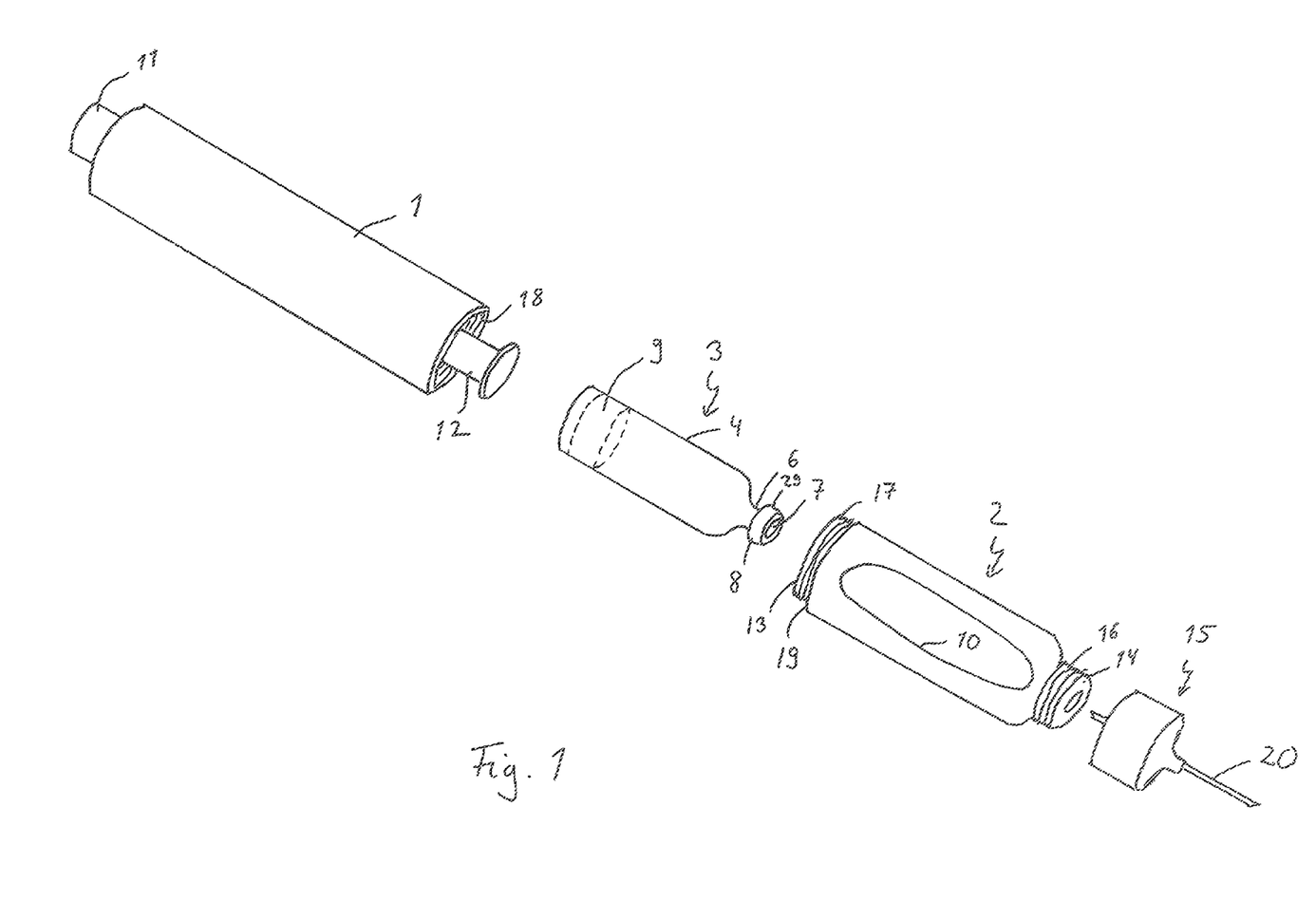
FIG. 1 shows an exploded view of an embodiment of a drug delivery device.

FIG. 1 shows an exploded view of an embodiment of a drug delivery device. The drug delivery device comprises a body member 1, a cartridge holder 2 in which a cartridge 3 is inserted and a needle unit 15.

The cartridge 3 which contains a drug has a body portion 4 which is essentially cylindrically formed. A label 5 may be positioned on the body portion 4, the label 5 providing information about the drug inside the cartridge 3, for example. The cartridge 3 is narrowed between the distal end of the cartridge which is formed as skirt 29 and the body portion 4. The narrowed portion is a neck portion 6. A septum 7 is located at the distal end of the cartridge 3, the septum 7 being fixed by a flanged rim 8. The septum 7 can be punctured by a cannula 20 and may be made of rubber.

A bung 9 is located inside the cartridge 3. Initially the bung 9 is located at the proximal end of the cartridge 3. The bung 9 is distally displaceable along the inside wall of the cartridge 3. In one embodiment the cartridge 3 is transparent or semitransparent, for example made of glass, so that the bung 9 inside the cartridge 3 is visible, thereby indicating the amount of remaining drug in the cartridge.

The cartridge holder 2 is suitable for holding the cartridge 3. The cartridge holder 2 has a window 10, which may be formed as cut-out in the cartridge holder 2. The cartridge 3 inside the cartridge holder 2 is visible through the window 10.

The cartridge holder 2 is attachable to the body member 1 by means of a connecting piece 13 located at the proximal end of the cartridge holder 2. In this embodiment the connecting piece 13 is essentially tubular. An outer thread 17 is located on the outside wall of the connecting piece 13. Distally beneath the connecting piece 13 a step which serves as stop 19 is formed.

A needle hub 14 which can be coupled with a needle unit 15 is provided at the distal end of the cartridge holder 3. In this embodiment the needle hub 14 comprises an outer thread 16 which can be threadedly connected to an inner thread (not shown) of the needle unit 15. In an alternative embodiment (not shown) the needle hub 14 and the needle unit 15 are connected by clipping means or any other suitable connection means.

The needle unit 15 can be attached to the needle hub 14. The needle unit 15 comprises a cannula 20 which punctures the septum 7 of the cartridge 3 when the needle unit 15 is being attached to the needle hub 14.

In this embodiment the body member 1 and the cartridge holder 2 form proximal and distal parts of the housing, respectively. The housing may be designed to enable safe, correct, and comfortable handling of the drug delivery device.

The body member 1 houses and protects a dose setting and delivery mechanism which is located in the body member 1. The body member 1 is essentially tubular shaped and comprises an inner thread 18 located on the distal inside wall of the body member 1. During assembling, the body member 1 is screwed to the connecting piece 13 until the distal edge of the body member 1 reaches the stop 19 so that the body member 1 is threadedly connected with the cartridge holder 2. In an alternative embodiment (not shown) the body member 1 and the cartridge holder 2 are connected by clipping means or any other suitable connection means.

The dose setting and delivery mechanism (not explicitly shown) comprises a button member 11 which is suitable for selecting a dose of a drug, by rotationally moving the button member 11 for example, and for initiating the drug delivery, by pushing the button member 11 distally with respect to the body member 1 for example. An alternative embodiment of the dose setting and delivery mechanism (not shown) may comprise a rotational dose setting sleeve which is used for setting the dose and a button member which is used for delivery.

The dose setting and delivery mechanism comprises a piston rod 12 located in the body member 1 of the drug delivery device, the piston rod 12 being moveable in the distal direction with respect to the body member 1. The bung 9 is displaced distally along the inside wall of the cartridge 3 when the piston rod 12 advanced in the distal direction, thereby dispelling the drug through the cannula 20.

When the drug delivery device is assembled or parts of the drug delivery device, e.g. the cartridge 3, are exchanged, the parts of the dose setting and delivery mechanism shall be positioned in a predetermined position with respect to the cartridge 3 or the housing of the drug delivery device. If the parts are positioned in the predetermined position, which includes that the piston rod 12 contacts the bung 9, this ensures that a predetermined dose is delivered when the drug delivery device is used. Fixing members (not shown in FIG. 1) which are described below are provided for securing the cartridge in its predetermined position. The cartridge 3 is secured against axial displacement, especially against distal displacement, so that the bung 9 remains in contact with the piston rod 12.

Figure 2:
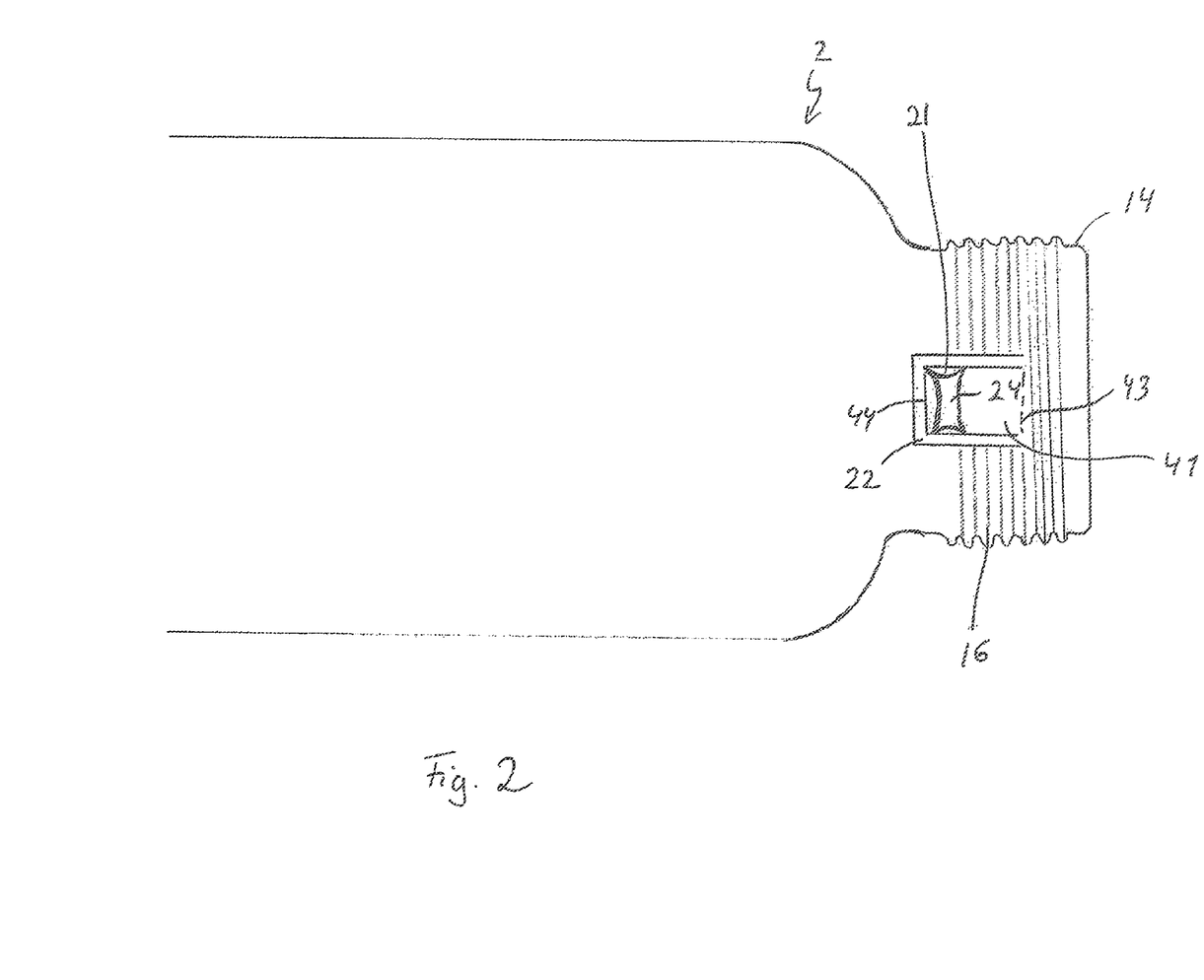
FIG. 2 shows a view of an embodiment of a cartridge holder.

FIG. 2 shows an embodiment of a cartridge holder 3. The distal part of the cartridge holder 3 is formed as needle hub 14 in which the neck portion 6 and the skirt 29 of the cartridge (not shown in FIG. 2) can be placed. The needle hub 14 comprises an outer thread 16 suitable for coupling the needle hub 14 with the needle unit 15 (not shown in FIG. 2).

Two fixing members 21 are located on opposite sides of the needle hub 14, which means that the fixing members 21 are set up at a 180 degree angle to one another. In FIG. 2 only one of the fixing members 21 is visible. The fixing member 21 which has an outer side 41 and an inner side 42 (not shown in FIG. 2 but in FIG. 3) is located in an opening of the needle hub 14 and connected with the needle hub 14, so that the fixing member 21 is moveable radially inwardly from a first position to a second position. When a force impacts to the outer side 41 of the fixing member 21, the inner side 42 of the fixing member 21 is moved towards the cartridge 3 which is located inside the cartridge holder 2.

In this embodiment the fixing member 21 is flexible and integrally formed with the needle hub 14. The fixing member is formed as spring arm. The fixing member 21 has the outer side 41, the inner side 42 (not shown in FIG. 2 but in FIG. 3) and a side 43 which is connected with the needle hub 14. An edge 44 of the fixing member 21 extends from one end of the side 43 which is connected with the needle hub 14 to the other end of this side, wherein the edge 43 is separated from the needle hub 14 by a cut-out 22. The cut-out 22 may be U-shaped, V-shaped or may have any form which is suitable for forming the spring arm. In this embodiment the cut-out separates the rectangular fixing member 21 from the needle hub 14. In other words, the fixing member 21 is a wall section of the needle hub 14 which can be bent radially inwardly. In an alternative embodiment (not shown) the fixing member 21 is connected to the needle hub 14 by means of a hinge.

The fixing member 21 comprises a first protrusion 24 on which a force can impact so that the fixing member 21 is bent inwardly. In a first state, which means that the needle unit 15 is not attached to the needle hub 14, the fixing member is positioned in a first position in which the first protrusion 24 protrudes over the ribs of the thread 16.

In the second state the flexible fixing member 21 is suitable to secure the cartridge 3 against axial displacement. During attachment of the needle unit 15 the needle hub 14 is inserted to the needle unit 15, thereby the inner wall of the needle unit 15 abuts on the first protrusions 24 of the fixing member 21 so that the fixing members 21 are pushed radially inwardly from the first positions to second positions in which the first protrusions 24 are aligned with the outer surface of thread 16.

Figure 3:
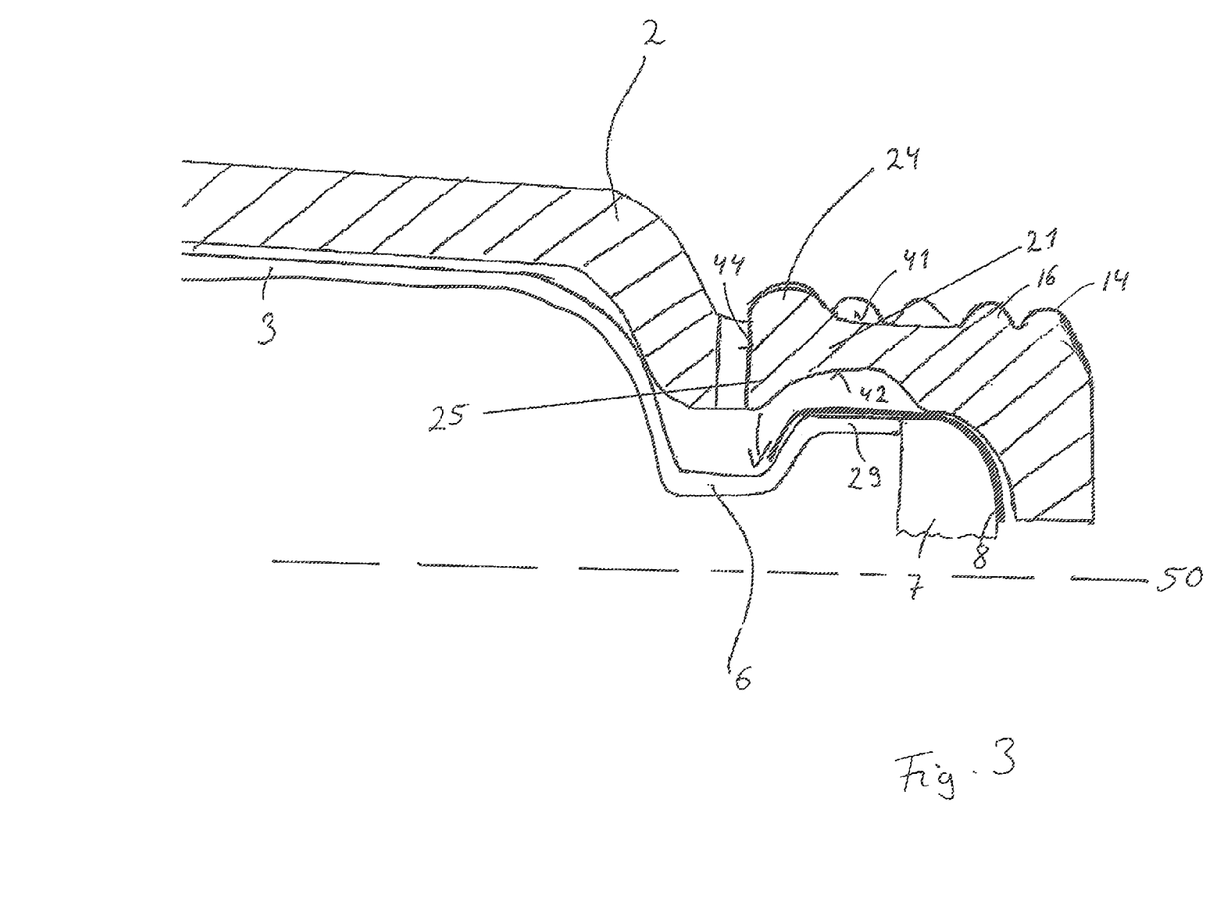
FIG. 3 shows a sectional detailed view of the distal portion of a cartridge and the cartridge holder which is shown in FIG. 2.

FIG. 3 shows a detailed sectional view of the distal portion of the cartridge 3 and the cartridge holder 2 which are shown in FIG. 2. For clarity reasons the distal portions of the cartridge 3 and the cartridge holder 2, which are symmetrical, are shown merely above the longitudinal axis 50 of the cartridge holder 2.

The cartridge holder 2 is configured to hold the cartridge 3 so that the distal part of the cartridge 3, which includes the skirt 29, is placed inside the needle hub 14.

The fixing member 21 is integrally formed with the needle hub 14 and comprises the first protrusion 24 which extends radially outwardly, the first protrusion 24 protruding over the helically running ribs of the thread 16.

The fixing member 21 further comprises a catch portion 25 formed on the inner side 42 of the fixing member 21. The catch portion 25 is configured to secure the cartridge 3 against distal displacement when the fixing member 21 is bent radially inwards. One embodiment of the catch portion 25 has a concave profile, which matches with the profile of the distal portion of the cartridge 3, so that the catch portion 25 is positioned behind the skirt 29 of the cartridge, which means that the catch portion 25 lies on the proximal edge of the skirt 29 or the flanged rim 8 and at least partly engages with the neck portion 6. Partly engages means that the catch portion 25 extends radially inwardly with respect to the skirt 29 when the fixing member 25 is moved inwardly. In one embodiment the inner side 42 of the fixing member 21 is sloped so that it matches or substantially matches with the button edge of the flanged rim 8.

When the needle unit 15 is attached to the needle hub 14, the first protrusion 24, which protrudes over the thread 16, is pushed by the inner wall of the needle unit 15 radially inwardly so that the first protrusion 24 is aligned with the ribs of the thread 16. The slope of the catch portion 25 lies behind the button edge of the flanged rim 8 when the fixing member is bent radially inwardly, thereby fixing and securing the cartridge 3 against axial displacement.

Figure 4:
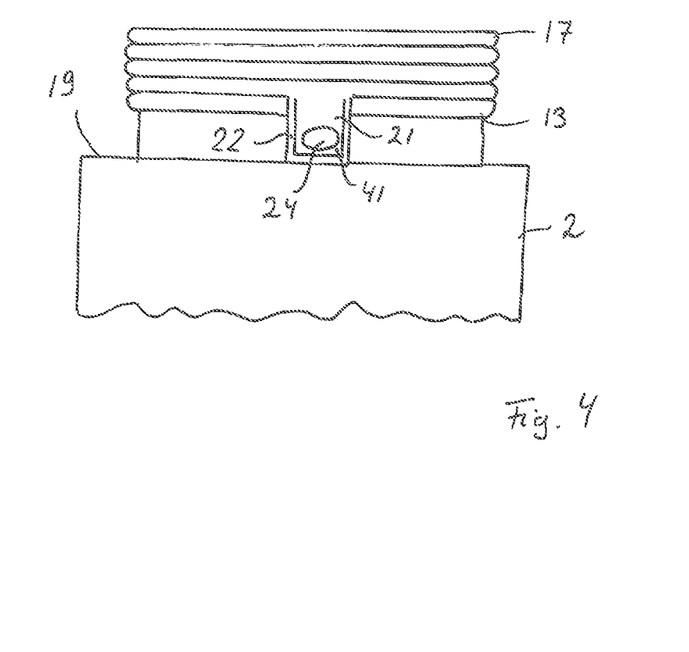
FIG. 4 shows a detailed view of the proximal part of an embodiment of a cartridge holder.

FIG. 4 shows a detailed view of the proximal part of an embodiment of the cartridge holder 2.

The proximal part of the cartridge holder 2 is configured to be inserted to the body member 1 (not shown in FIG. 4). An outer thread 17 formed by a helical structure is located on the connecting piece 13 which is located at the proximal end of the cartridge holder 2.

The connecting piece 13 comprises two fixing members 21 which are set up at a 180 degree angle to one another. In FIG. 4 only one of the fixing members 21 is visible. The fixing member 21 which has an outer side 41 and an inner side 42 (not shown in FIG. 4) is located in an opening of the connecting piece 13 and is connected with the connecting piece 13, so that the fixing member 21 is moveable inwardly from the first position to the second position. Thus the inner side 42 of the fixing member 21 is moved towards to cartridge 3 (not shown in FIG. 4) located inside the cartridge holder 2 when a force impacts on the outer side 41 of the fixing member 21. In this embodiment the fixing member 21 is flexible and integrally formed with the connecting piece 13. The fixing member 21 is formed as spring arm which is separated from the connecting piece 13 by a U-shaped cut-out 22. In an alternative embodiment (not shown) the fixing member is connected to the needle hub 14 by means of a hinge.

The fixing member 21 comprises a first protrusion 24 on which a force can impact so that the fixing member 21 is bent inwardly. In the first position, which means that the needle unit 15 is not attached to the needle hub 14, the fixing member 21 is positioned so that the first protrusion 24 protrudes over the ribs of the thread 17.

In the second position the flexible fixing member 21 is suitable to secure the cartridge 3 against axial displacement. When the body member 1 is being attached to the connecting piece 13, the connecting piece 13 is inserted in the body member 1, thereby the inner wall of the body member 1 abuts on the first protrusion 24 of the fixing members 21 so that the fixing members 21 are pushed radially inwardly to the second position in which the first protrusions 24 is aligned with the ribs of the thread 17.

Figure 5:
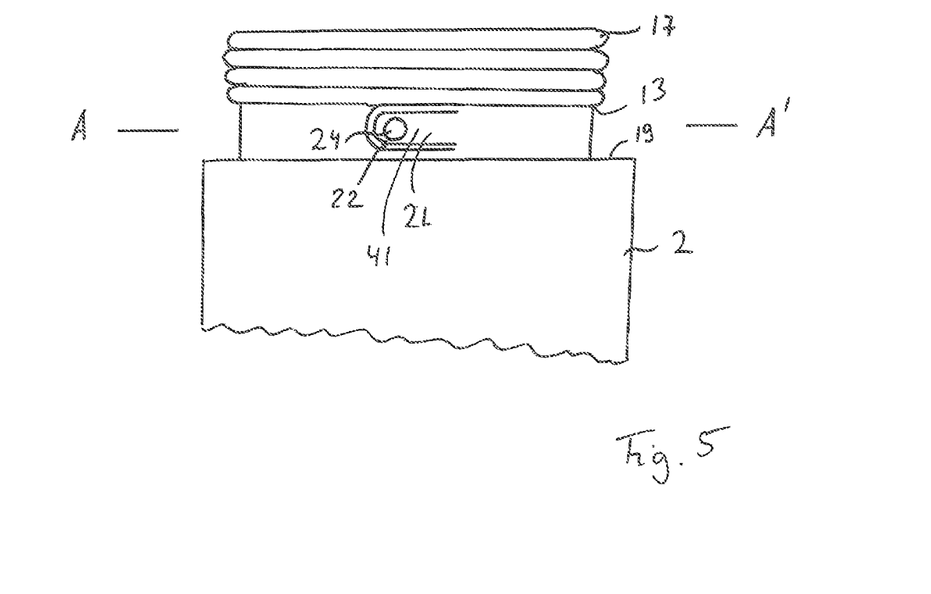
FIG. 5 shows a detailed view of the proximal part of another embodiment of a cartridge holder.

FIG. 5 shows a detailed view of the proximal part of an alternative embodiment of the cartridge holder 3.

This embodiment is similar to the one shown in FIG. 4. In this embodiment the fixing member is formed as spring arm which is positioned orthogonal to the longitudinal axis of the cartridge holder 3. Contrary to that, the embodiment shown in FIG. 4 has a spring arm which is positioned parallel to the longitudinal axis.

Figure 6:
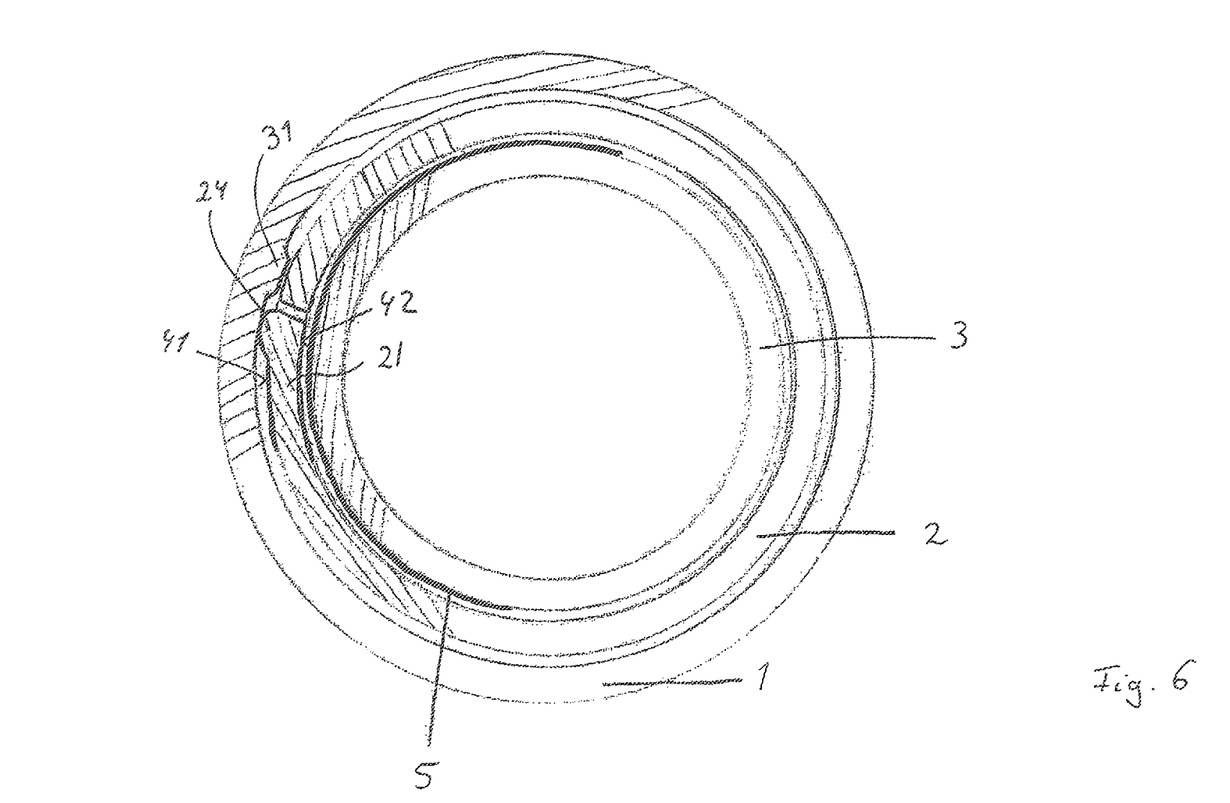
FIG. 6 shows a sectional view of the cartridge holder which is shown in FIG. 5 and a body member during attachment.

FIG. 6 shows a sectional view of the cartridge holder 2 which is shown in FIG. 5 during attachment along the line A-A'. For clarity reason only one of the fixing members 21 is shown in FIG. 6.

FIG. 6 shows the cartridge holder 2 in which the cartridge 3 is inserted during attachment, which means that the connecting piece 13 of the cartridge holder 2 is being inserted in the body member 1 by screwing. The body member 1 has not reached the stop 19 (not shown in FIG. 6).

In a first state, which is the state during attachment, the inner side 42 of the fixing member 21 is aligned with the inner wall of the connecting piece 13, so that the cartridge 3 can be inserted in the cartridge holder 2. The fixing member 21 comprises a first protrusion 24 which protrudes over the thread 17.

The body member 1 comprises second protrusions 31 located on the inside wall of the body member 1. The positions of the second protrusions 31 are matched with positions of the first protrusions 24. The second protrusions 31 are configured so that the first protrusions 24 of the fixing member 21 are pushed radially inwardly when the second protrusion 31 of the body member 1 abuts on the first protrusion 24 of the connecting piece 13. The first and second protrusions 24, 31 may be sloped or rounded, so that the second protrusions 31 slide onto the first protrusions 24 when the body member 2 is reaching its final position, which means that the distal edge of the body member 1 reaches the stop 19 (not shown in FIG. 6).

Figure 7:
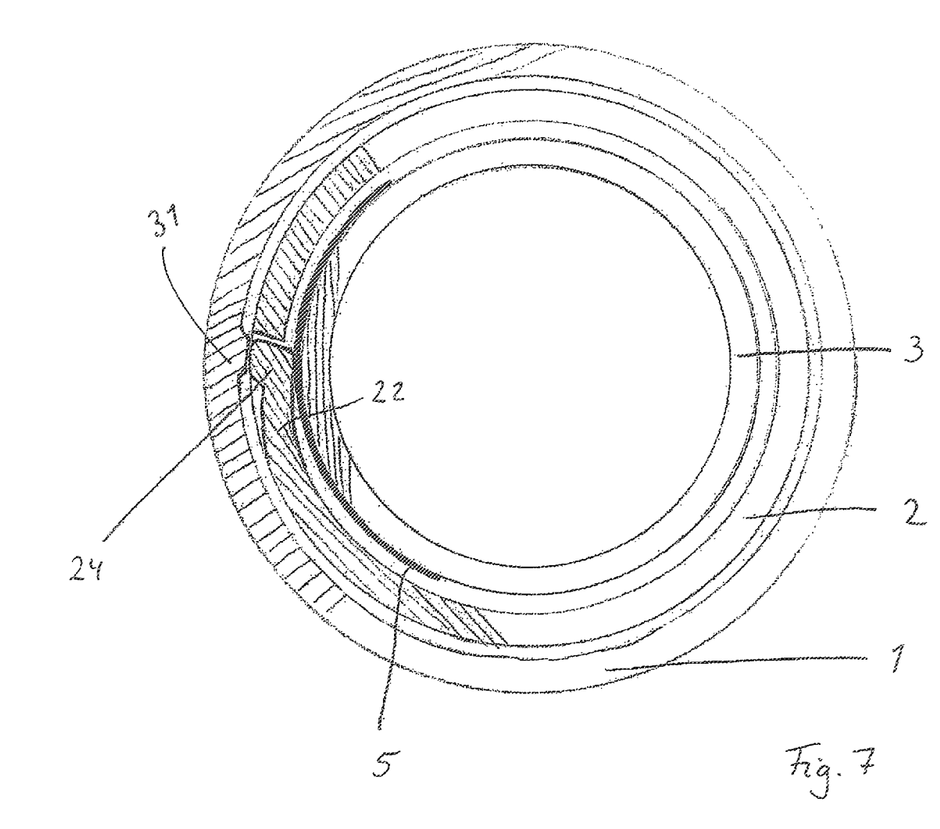
FIG. 7 shows a sectional view of the cartridge holder and the body member which are shown in FIG. 6 after attachment.

FIG. 7 shows a sectional view of the cartridge holder 2 and the body member 1 which are shown in FIG. 6 after attachment.

The body member 1 has reached its final position. The second protrusion 31 of the body member 1 abuts on the first protrusion 24 of the fixing member 21 so that the fixing member 21 is bent radially inwardly, thereby the inner side 42 of the fixing member 21 abuts on the cartridge 3 so that it is secured against axial, especially distal, displacement. In this embodiment the cartridge 3 is secured in a force fitting manner. In other words, the inner side 42 of the flexible member 21 impacts a force on the cartridge 3 so that it is hold in its position.

In one embodiment the inner side 42 of the fixing member 21 is roughened so that the friction between the fixing member 21 and the cartridge 3 is increased. In one embodiment the cartridge 3 has a roughened surface or roughened portions on the surface on which the inner side 42 of the flexible member 21 abuts. In the embodiment shown in FIGS. 6 and 7 the inner side 42 of the flexible member 21 abuts on the label 5 positioned on the cartridge 3. The surface of the label 5 may be rougher than the surface of the cartridge 3, for example the cartridge 3 is made of glass and the label 5 is made of paper.

In one embodiment the inner side 42 of the fixing member 21 comprises a radially inwardly protruding element (not shown in FIGS. 6 and 7) which impacts the radial force on the cartridge 3. Thus, the force caused by the inwardly bent fixing member 21 radially impacts on the cartridge 3 at the point where the protruding element touches the cartridge 3.

In this embodiment the inner side 41 of the fixing member 21 is pushed towards the cartridge 3, thereby securing the cartridge 3 against axial displacement. The cartridge 3 is secured by frictional connection. Alternatively or additionally, the cartridge 3 may be secured by a positive locking. In one embodiment the inner side 42 of the fixing member 21 is pushed into a cavity provided in the cartridge 3 (not shown).

Other implementations are within the scope of the claims. Elements of different embodiments may be combined to form implementations not specifically described herein.

The invention claimed is:

1. A cartridge holder having a distal end and a proximal end, the cartridge holder comprising:
   a connecting piece located at the proximal end having a connector that attaches to a body member of a drug delivery device containing a dose delivery mechanism;
   a needle hub located at the distal end that attaches to a needle unit, where the needle hub and connecting piece are part of a single housing;
   wherein the needle hub is a coupling housing portion in which a cartridge can be inserted at least partly, the coupling housing portion having an outer surface having a cut-out portion that defines a fixing member that is integral with a portion of the outer surface, the portion of the outer surface being adjacent to the fixing member in a circumferential direction of the cartridge holder, and where the fixing member has a first position and an inner surface and a protrusion that projects radially outward from the portion of the outer surface, where the fixing member is bent radially inward to a second position while the portion of the outer surface remains in its initial position when a radially directed contact force is applied to the protrusion by the body member or the needle unit when the connecting piece attaches to the body member or when the needle unit attaches to the needle hub such that the fixing member and the protrusion moves radially inwardly such that the inner surface of the fixing member is caused to directly engage and contact the cartridge to secure the cartridge against distal displacement of the cartridge relative to cartridge holder.

2. The cartridge holder according to claim 1, wherein the fixing member is flexible.

3. The cartridge holder according to claim 1, wherein the fixing member has a side which is connected with the coupling housing portion, an edge of the fixing member extending from one end of the side which is connected with the coupling housing portion to the other end of this side, the edge being separated from the coupling housing portion by the cut-out.

4. The cartridge holder according to claim 1, wherein the fixing member comprises a catch portion formed on an inner side of the fixing member.

5. The cartridge holder according to claim 1, wherein the coupling housing portion comprises a thread.

6. The cartridge holder of claim 1 where the fixing member in the first position is positioned within the cut-out such that the portion of the outer surface and the outer surface are in alignment.

7. The cartridge holder of claim 1 where when the fixing member is in the second position, the portion of the outer surface is no longer aligned with the outer surface.

8. A drug delivery device comprising a cartridge holder according to claim 1 and further comprising a cartridge which is located in the cartridge holder, wherein a needle unit of the drug delivery device is coupled with the coupling housing portion, thereby the needle unit of the drug delivery device abuts on the fixing member so that the fixing member secures the cartridge against distal displacement.

9. The drug delivery device according to claim 8, wherein the coupling housing portion is inserted in the needle unit of the drug delivery device.

10. The drug delivery device according to claim 8, wherein the needle unit of the drug delivery device comprises a second protrusion which abuts on the fixing member.

11. The drug delivery device according to claim 8, wherein the fixing member is configured to at least partly engage with a cavity provided in the cartridge or a necking of the cartridge.

12. The drug delivery device according to claim 11, wherein the cartridge has a neck portion and a skirt which radially protrudes over the neck portion, the fixing member being configured to engage at least partly with the neck portion.

13. The drug delivery device according to claim 8, wherein the fixing member abuts on the cartridge so that a force-fit connection is formed.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35
```